United States Patent
Kolln

(10) Patent No.: US 9,267,498 B2
(45) Date of Patent: Feb. 23, 2016

(54) CONTINUOUSLY CONVEYING INFUSION PUMP

(76) Inventor: Harm Kolln, Kiel (DE)

(*) Notice: Subject to any disclaimer, the term of this patent is extended or adjusted under 35 U.S.C. 154(b) by 412 days.

(21) Appl. No.: 13/512,720

(22) PCT Filed: Dec. 10, 2010

(86) PCT No.: PCT/DE2010/001438
§ 371 (c)(1),
(2), (4) Date: May 30, 2012

(87) PCT Pub. No.: WO2011/069494
PCT Pub. Date: Jun. 16, 2011

(65) Prior Publication Data
US 2012/0265128 A1 Oct. 18, 2012

(30) Foreign Application Priority Data
Dec. 11, 2009 (DE) .......................... 10 2009 057 792

(51) Int. Cl.
| A61M 5/168 | (2006.01) |
| F04B 25/00 | (2006.01) |
| A61M 5/142 | (2006.01) |
| A61M 5/36 | (2006.01) |
| F04B 1/02 | (2006.01) |
| F04B 7/00 | (2006.01) |

(Continued)

(52) U.S. Cl.
CPC ............ F04B 25/005 (2013.01); A61M 5/1422 (2013.01); A61M 5/14216 (2013.01); A61M 5/365 (2013.01); F04B 1/02 (2013.01); F04B 7/0003 (2013.01); F04B 7/0007 (2013.01); F04B 3/00 (2013.01)

(58) Field of Classification Search
CPC ............ A61M 5/14216; A61M 5/1422; F04B 7/0007; F04B 7/0003; F04B 25/005; F04B 1/02; F04B 3/00
USPC ................ 417/521, 560, 519, 285, 298, 300, 417/410.3; 137/625.21, 625.22; 604/67, 604/132, 131
See application file for complete search history.

(56) References Cited

U.S. PATENT DOCUMENTS 4,627,419 A * 12/1986 Hills ..................... A61M 1/106
128/DIG. 12
4,808,077 A * 2/1989 Kan .................... F04B 11/0075
417/18

(Continued)

FOREIGN PATENT DOCUMENTS

EP 0458114 11/1991
WO WO 2008/141337 11/2008

Primary Examiner — Bhisma Mehta
Assistant Examiner — Jenna Zhang
(74) Attorney, Agent, or Firm — Diederiks & Whitelaw, PLC

(57) ABSTRACT

An infusion pump for continuously conveying a fluid includes an inlet, an outlet, a first piston movably supported in a first chamber connected to the inlet, a second piston movably supported in a second chamber connected to the outlet, and a connecting channel connecting the first chamber to the second chamber. At least one control element, in a first position, connects the inlet to the first chamber and, in a second position, connects the first chamber to the second chamber. A controller acts upon the first piston, the second piston, and the control element so that, when the control element is set in the first position, the first chamber is filled while the second chamber is drained, and when in the second position, the first chamber is drained and the second chamber is filled, wherein a constant discharge at the outlet is maintained at a predefined flow rate.

20 Claims, 3 Drawing Sheets

(51) Int. Cl.
*A61M 5/145* (2006.01)
*F04B 3/00* (2006.01)

(56) References Cited

U.S. PATENT DOCUMENTS

| | | | |
|---|---|---|---|
| 6,183,211 B1 * | 2/2001 | Wood | F04B 25/005 417/246 |
| 6,203,528 B1 * | 3/2001 | Deckert | A61M 5/142 604/131 |
| 2005/0002806 A1 * | 1/2005 | Fuechslin | A61M 39/223 417/416 |
| 2005/0197645 A1 * | 9/2005 | Karpowicz | A61M 1/0062 604/514 |
| 2007/0083160 A1 * | 4/2007 | Hall | A61B 5/1427 604/131 |
| 2007/0261553 A1 | 11/2007 | Gerner | |
| 2008/0287872 A1 * | 11/2008 | Patzer | A61M 5/1413 604/131 |

* cited by examiner

CONTINUOUSLY CONVEYING INFUSION PUMP

CROSS-REFERENCE TO RELATED APPLICATIONS

This application represents a National Stage application of PCT/DE2010/0014368 entitled "Continuously Conveying Infusion Pump" filed Dec. 10, 2010, pending.

BACKGROUND OF THE INVENTION

The invention relates to an infusion fusion pump for continually conveying a fluid, comprising an inlet, an outlet, a first piston movably supported in a first chamber, and a second piston movably supported in a second chamber. The invention relates in particular to an infusion pump, using which very small amounts of a drug can be applied precisely and with a constantly uniform flow or conveying rate.

EP 045 8114 B1 already discloses an infusion pump where using four valves two cylinders in each case equipped with a piston can alternately be filled with a drug from a reservoir and the drug can be drained by discharging the drug to the patient. Switching over the drug supply from a drained to a filled cylinder can achieve an approximately continuous conveying of drugs with relatively simple means.

A disadvantage of this infusion pump however is that due to the valve clearance an additional volume is created in the valve when the valve is opened, there being a reduced conveying of the drug. On the other hand, this reduced volume is displaced again when the valve is closed, resulting in increased conveying.

Over longer periods, the drug delivery corresponds to the therapy plan established by the physician. Under certain circumstances however, only a temporally brief under or oversupply of the patient with the drug conveyed by the infusion pump can—as a function of the drug—lead to the desired therapeutic success not being achieved.

SUMMARY OF THE INVENTION

It is therefore the object of the invention to provide an infusion pump, using which even very small amounts of liquid, preferably in the microliter range, can conveyed with a high degree of precision and continuously.

The continuously conveying infusion pump according to the invention ensures, as a result of the arrangement of the first chamber designated as conveying chamber and the second chamber designated as equalisation chamber together with volume-neutral valves, that the drug release is only dependent on the control of the actuators of the previously mentioned elements and is thus continuous at each desired conveying rate, the control cycles being identical.

BRIEF DESCRIPTION OF THE DRAWINGS

The invention is explained in more detail with reference to an exemplary embodiment of particularly preferred design, in which.

DETAILED DESCRIPTION OF THE INVENTION

Figure 1:
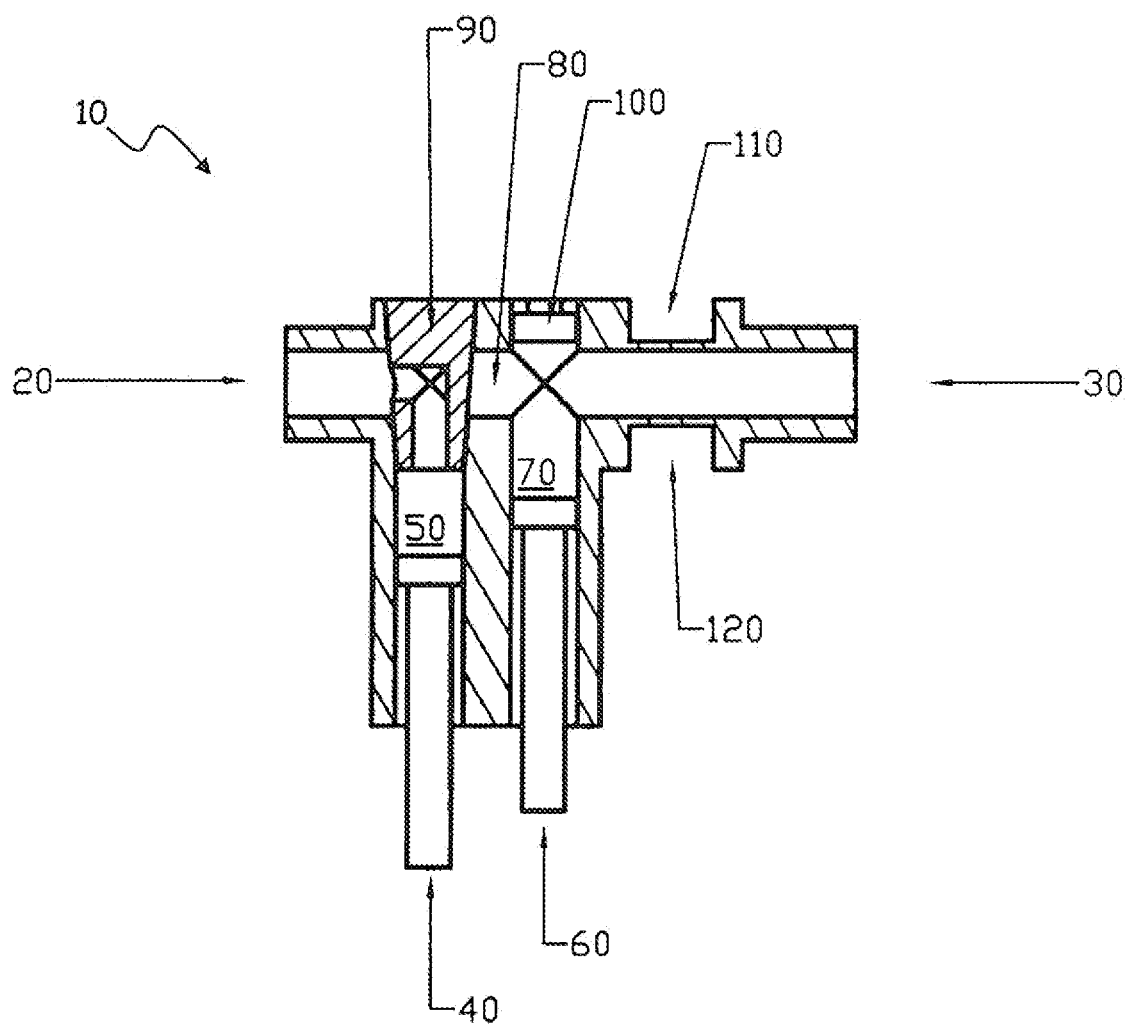
FIG. 1 shows a schematic sectional view through a particularly preferred exemplary embodiment of the inventive infusion pump.

FIG. 1 shows a schematic sectional view through a particularly preferred exemplary embodiment of the infusion pump according to the invention. The infusion pump 10 exhibits an inlet 20 for introducing a fluid, for example a drug, from a reservoir (not shown) into the infusion pump 10, and an outlet 30 that passes on the fluid from the infusion pump 10 to the patient. The inlet 20 and the outlet 30 of the infusion pump are arranged, preferably aligned, at mutually opposite sides of the infusion pump 10.

The infusion pump 10 exhibits a first chamber 50 with a first piston 40 and a second chamber 70 adjacent preferably parallel, subsequent in the flow direction, with a second piston 60, the first chamber 50 and the first piston 40 also been designated as conveying chamber 50 or equalisation piston 60, and the second piston 60 also being designated as equalisation chamber 70 and equalisation piston 60. The first chamber 50 is connected to the inlet 20 (or an intake channel) whereas the second chamber 70 is connected to the outlet 30 (or an exhaust channel). The chambers 50, 70 are mutually connected by a connecting channel 80, the connecting channel 80 preferably being arranged such that it is aligned to the outlet 30. In a particularly preferred manner the inlet 20, the connecting channel 80 and the outlet 30 are arranged such that they are aligned.

The pistons 40, 60 are movably supported in the first chamber 50, designated as conveying chamber, or the second chamber 70, designated as equalisation chamber, the intermediate space between the pistons 40, 60 and the inside wall of the chambers 50, 70 being, if necessary, sealed with suitable means. The piston pumps that are formed by the pistons 40, 60 in the chambers 50, 70 are actuated by means of suitable actuators (not illustrated).

According to the invention, a control element 90 is provided that is preferably designed as a two-way cock, the sleeve of the cock 90 being preferably formed by the housing of the infusion pump 10. The plug of the cock 90 is sealingly supported in the sleeve. The plug can also be designed as part of a three-way cock, so that for exerting the function of the control element 90, only a small rotation of the three-way cock through a few angular degrees is necessary.

Figure 2:
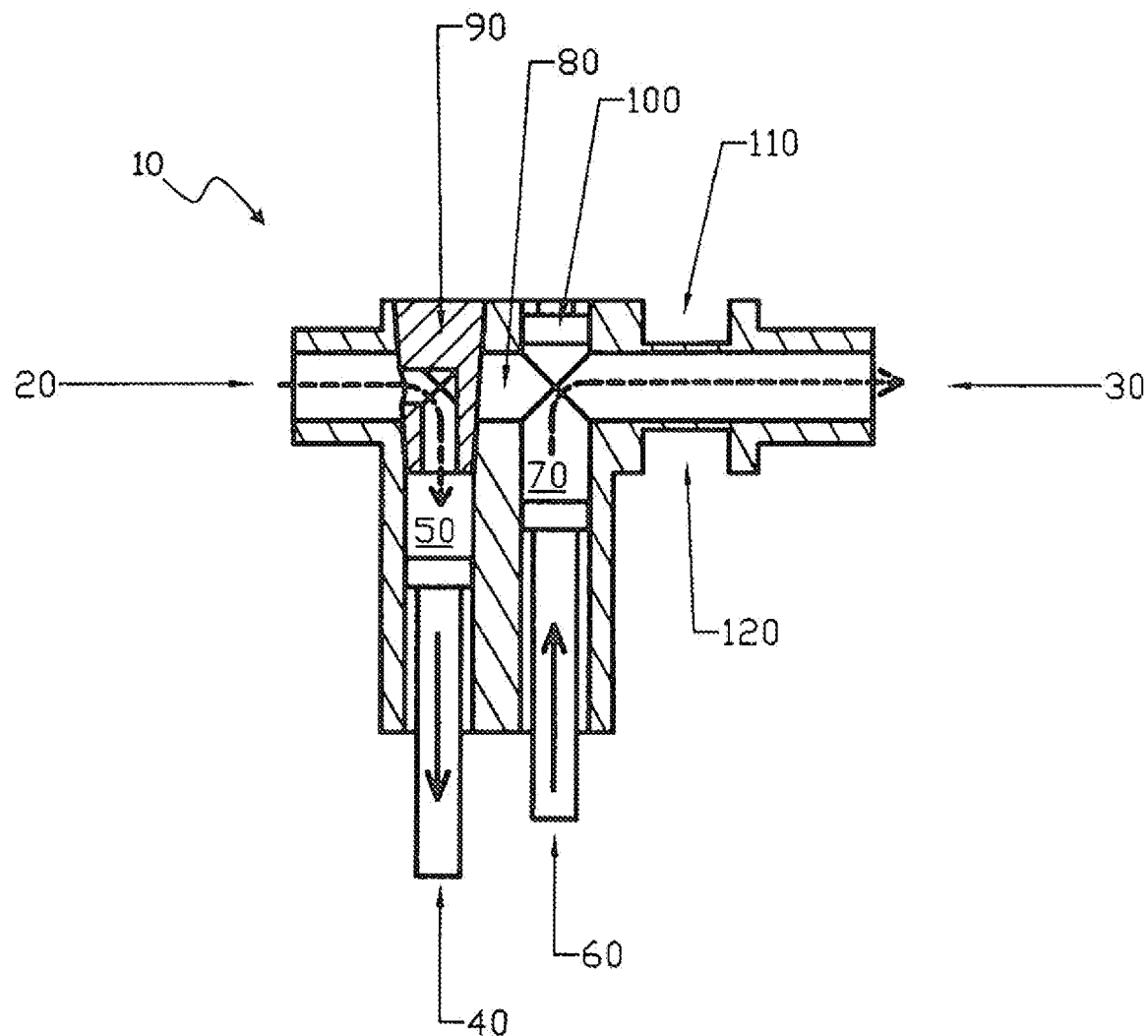
FIG. 2 shows a schematic sectional view of the infusion pump from FIG. 1 in a first switching state.

That is to say, the control element 90 is designed such that in a first position of the control elements 90 the inlet 20 is connected to the first chamber 50 in a communicating manner, whereas the communication between the first chamber 50 and the second chamber 70 is blocked by the control element 90. In this position, the first chamber 50 can be filled from the reservoir by a downwards movement of the first piston 40, and the second chamber 70 can pass on its content by means of an upwards movement of the second piston 60 to the patient through the outlet 30 in a continually conveying manner (see FIG. 2).

Figure 3:
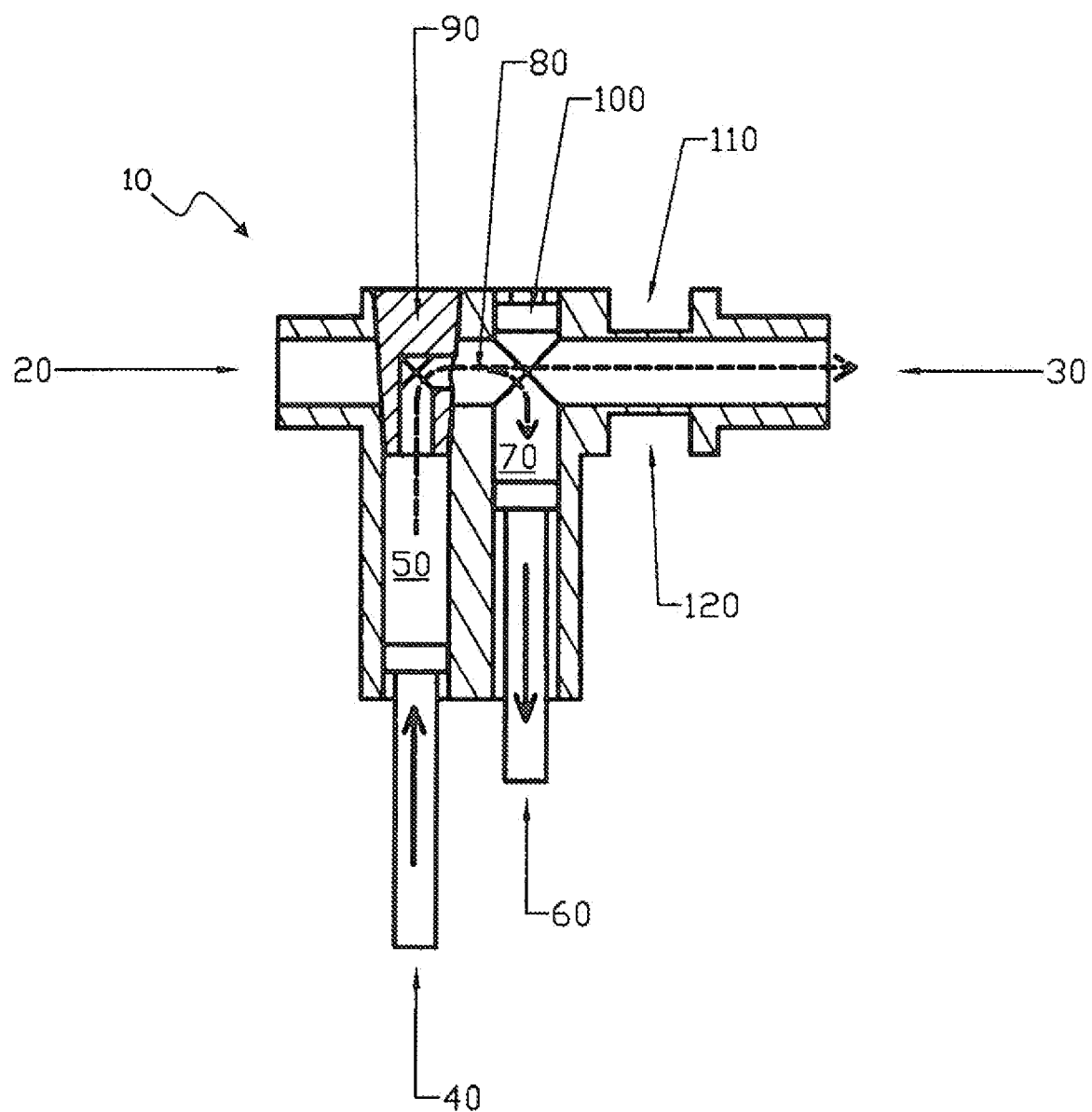
FIG. 3A shows a schematic sectional view of the infusion pump from FIG. 1 in a second switching state.

In a second position, for example rotated through 180°, of the two-way cock 90 (or its plug 90), the communication between the inlet 20 and the first chamber 50 is blocked by the plug 90, however a communication between the first chamber 50 and the second chamber 70 being produced via the connecting channel 80. The upwards movement of the first piston 40 conducts the fluid, that has been displaced from the first chamber 50, into the second chamber 70 that is filled during a simultaneous downwards movement of the second piston 60 (see FIG. 3).

As an alternative, the control element can also be provided by two valves (not shown) instead of the cock 90, a first valve being arranged between the inlet and the first chamber and second valve being arranged between the first chamber and the second chamber. In the process, the valves are switched alternately, so that the two valves assume the function of the cock shown above.

As a further preferred design of the alternative it can be envisaged that the first valve is designed as a non-return valve and the second valve as a valve that is actuated by an actuator. Again as a particularly preferred alternative for this design, the first valve can be designed as a non-return valve and the second valve as a siphon that preferably does not open until a differential pressure of >100 hPa.

Here the movements of the two pistons 40, 60 are coordinated by a control system (not shown) such that the differential volume that is produced by draining the first chamber 50 and filling the second chamber 70 and is ejected corresponds to that volume that is required for continually conveying the desired medication. The continuity of the conveying action ensures that the drug is always infused under pressure into the tissue, as is demanded for example by the "Convection Enhanced Delivery" (CED) method.

In the exemplary embodiment, the connected unit is designed as a piston 100 to be connected for pressure measurement purposes. The piston 100 is seated on a suitable force sensor (not shown), for example a cantilevered beam. From the force with which this piston 100 is held in its position, the pressure in the equalisation chamber 70 that is connected to the outflow channel 30 can be determined taking into account the piston surface. As an alternative, instead of the previously mentioned movably supported third piston 100 it is also possible to use an inflatable/deflatable membrane for pressure measurement purposes. The pressure measurement is necessary for example to detect an occlusion, it is being provided in the case of a pressure rise above a predetermined value that an alarm is emitted.

Finally, there is also provided an area 110, 120 for connecting to the infusion pump a detector for bubble detection in the fluid. Bubble detection can for example be provided by means of ultrasound measurement at a frequency in the MHz range or by optical measurement utilising the different indices of refraction of liquid and gas. To this end, a receiving chamber 110 for the sound or light transmitter and a receiving chamber 120 for the sound or light receiver are integrated into the pump carrier of the infusion pump 10. In the exemplary embodiment, the outlet 30 exhibits a rectangular cross-section for avoiding unwanted reflections or refractions of light or sound at boundary surfaces that are not even.

In summary, the method sequence of the infusion pump that is controlled by the control system is described once more:

The plug 90 closes the connecting channel 80 and has connected the conveying chamber 50 via the inlet 20 to the liquid supply (not shown). In this state, the equalisation piston 60 is forced inwards (i.e. upwards in the drawing plane) at the velocity that is necessary to continually convey the desired amount of liquid through the outlet 30. At the same time, the conveying piston 50 is pulled outwards (i.e. downwards in the drawing plane) at the maximum intended velocity. At the same time the conveying chamber 50 is filled with the fluid, e.g. a drug, from the liquid supply. Due to the closed connecting channel 80, these liquid streams are independent from each other. After, the supply chamber 50 is filled, the conveying piston 40 is no longer moved. After this the plug 90 in the exemplary embodiment is rotated through 180° until the inlet 20 is closed and the connecting channel 90 is open, while the equalisation piston 60 continues to be pushed inwards at a constant velocity. These procedures ensure that the outflow velocity of the fluid in the outlet 30 is not changed.

Then the conveying piston 40 is pushed inwards (i.e. upwards in the drawing plane) such that a larger amount of liquid is ejected from the conveying chamber 50 than is necessary for the constant conveying through the outlet 30. At the same time, the equalisation piston 60 is pulled outwards (i.e. downwards in the drawing plane) at the that velocity and thus the volume of the equalisation chamber 70 is increased, a fluid leaving the connecting channel 80 being taken up in the equalisation chamber 70 as a result. This takes place to the extent that is necessary to keep the outflow velocity of the liquid constant at the outlet 30.

After the conveying chamber 70 is drained, the conveying piston 40 is no longer moved and the equalisation piston 60 is again forced inwards (i.e. upwards in the drawing plane) at that velocity that is requisite to further maintain the constant outflow velocity of the fluid in the outlet 30. In the process, the fluid collected in the equalisation chamber 70 during the draining of the conveying chamber 40 is ejected.

Now the plug 90 is again rotated through 180° until the connecting channel 80 is closed and the conveying chamber 50 is connected to the inlet 20. Thereafter, the conveying piston 40 is again pulled outwards (i.e. downwards in the drawing plane) at the maximum intended velocity and the conveying chamber 50 is filled again and another control cycle sets in as described above. The continued ejection of liquid in the outlet 30 can in this way be maintained until the liquid supply to which the inlet is connected is exhausted.

As a result of the property of the inventive, continuously conveying infusion pump 10, that due to the construction in the exemplary embodiment at no time a situation can arise, where the free flow (uncontrolled drug flow on account of the pressure difference between the liquid supply and the patient access) is possible, additional measures in the case of a pressure difference as a result of gravity, temperature fluctuations or other influences can be dispensed with.

It is possible at any time to change the outflow velocity of the liquid between the minimum and maximum intended limits by correspondingly controlling the actuators. These limits are a function of the design of the pump 10, such as for example the performance of the selected actuators and dimensions of the pump that determine the size of the chambers 50, 70 and the diameters of the pistons 40, 60.

Finally, the invention also facilitates a design of the infusion pump 10 as a disposable product in a sterile embodiment. That is, the simple construction of the inventive infusion pump 10 facilitates the manufacture in the shape of an injection-moulded part, this facilitating cost-effective production and making it possible to use the infusion pump 10 as a disposable product.

Among others, the pump also complies with the requirement for supplying the drug directly into the brain tissue according to the "Convection Enhanced Delivery" (CED) method that exhibits great advantages compared to the non-continuous delivery of the drug.

The invention claimed is:

1. An infusion pump for continuously conveying a fluid, comprising
an inlet,
an outlet,
a first piston movably supported in a first chamber,
a second piston movably supported in a second chamber,
a connecting channel connecting the first chamber to the second chamber, the first chamber being connected to the inlet and the second chamber being connected to the outlet,
at least one control element movable between a first position and a second position wherein, when the at least one control element is in the first position, the inlet is in fluid communication with the first chamber while fluid communication between the first chamber and the second chamber is blocked and, when the at least one control element is in the second position, the first chamber is in fluid communication with the second chamber while fluid communication between the inlet and the first chamber is blocked, a controller that acts upon the first piston, the second piston, and the at least one control element so that, when the at least one control element is in the first position, the first chamber is filled while the second chamber is drained through the outlet at a predefined flow rate, and when the at least one control element is in the second position, the first chamber is drained and the second chamber is filled, wherein the infusion pump is configured such that a constant continuous discharge from the outlet is maintained at the predefined flow rate.

2. The infusion pump according to claim 1, wherein the at least one control element is a two-way or a three-way cock.

3. The infusion pump according to claim 2, wherein the at least one control element is formed by a first valve arranged between the inlet and the first chamber and a second valve arranged between the first chamber and the second chamber.

4. The infusion pump according to claim 2, further comprising a force sensor that detects a pressure in the second chamber or in the outlet.

5. The infusion pump according to claim 2, further comprising a detector having an ultrasound transmitter and an ultrasound receiver and/or a detector having a light source emitting light and a receiver detecting the light of the light source for detecting air bubbles in the fluid.

6. The infusion pump according to claim 1, wherein the at least one control element is formed by a first valve arranged between the inlet and the first chamber and a second valve arranged between the first chamber and the second chamber.

7. The infusion pump according to claim 6, wherein the first valve is a non-return valve.

8. The infusion pump according to claim 7, wherein the second valve is a siphon.

9. The infusion pump according to claim 8, further comprising a force sensor that detects a pressure in the second chamber or in the outlet.

10. The infusion pump according to claim 8, further comprising a detector having an ultrasound transmitter and an ultrasound receiver and/or a detector having a light source emitting light and a receiver detecting the light of the light source for detecting air bubbles in the fluid.

11. The infusion pump according to claim 7, further comprising a force sensor that detects a pressure in the second chamber or in the outlet.

12. The infusion pump according to claim 7, further comprising a detector having an ultrasound transmitter and an ultrasound receiver and/or a detector having a light source emitting light and a receiver detecting the light of the light source for detecting air bubbles in the fluid.

13. The infusion pump according to claim 6, further comprising a force sensor that detects a pressure in the second chamber or in the outlet.

14. The infusion pump according to claim 6, further comprising a detector having an ultrasound transmitter and an ultrasound receiver and/or a detector having a light source emitting light and a receiver detecting the light of the light source for detecting air bubbles in the fluid.

15. The infusion pump according to claim 6, further comprising a fluid reservoir connected to the inlet.

16. The infusion pump according to claim 1, further comprising a force sensor that detects a pressure in the second chamber or in the outlet.

17. The infusion pump according to claim 16, further comprising a detector having an ultrasound transmitter and an ultrasound receiver and/or a detector having a light source emitting light and a receiver detecting the light of the light source for detecting air bubbles in the fluid.

18. The infusion pump according to claim 1, further comprising a detector having an ultrasound transmitter and an ultrasound receiver and/or a detector having a light source emitting light and a receiver detecting light of the light source for detecting air bubbles in the fluid.

19. The infusion pump according to claim 18, wherein the detector is arranged between the second chamber and the outlet in a way interacting with the fluid.

20. The infusion pump according to claim 1, further comprising a fluid reservoir connected to the inlet.

* * * * *